United States Patent [19]

Jones et al.

[11] Patent Number: 5,621,118
[45] Date of Patent: Apr. 15, 1997

[54] OXIDATION PROCESS

[75] Inventors: Craig W. Jones, Whittle Hall; William R. Sanderson, Penketh; John P. Sankey, Latchford, all of United Kingdom

[73] Assignee: Solvay Interox Limited, Cheshire, England

[21] Appl. No.: 211,660

[22] PCT Filed: Oct. 14, 1992

[86] PCT No.: PCT/GB92/01879

§ 371 Date: Apr. 14, 1994

§ 102(e) Date: Apr. 14, 1994

[87] PCT Pub. No.: WO93/08144

PCT Pub. Date: Apr. 29, 1993

[30] Foreign Application Priority Data

Oct. 19, 1991 [GB] United Kingdom ........... 9122223

[51] Int. Cl.$^6$ ............ C07B 33/00; C07D 321/00; D21C 9/16
[52] U.S. Cl. ................ 549/200; 8/107; 8/101; 8/111; 549/330; 549/513; 549/523; 549/524; 568/27; 568/28; 564/298
[58] Field of Search ................ 8/107, 101, 111; 549/200, 330, 513, 523, 524; 423/513; 162/72, 76, 78, 82, 77; 568/27, 28; 564/298

[56] References Cited

U.S. PATENT DOCUMENTS 5,087,752 2/1992 Murray et al. .............. 564/298

Primary Examiner—Alan D. Diamond
Attorney, Agent, or Firm—Larson & Taylor

[57] ABSTRACT

A process for oxidizing a substrate susceptible to nucleophilic oxidation by reacting a bicaroate or monopersulfate solution with the substrate is disclosed. In one aspect, the substrate is introduced into the reaction mixture in an inert carrier gas, which can also serve to sweep the product out of the mixture. In a second aspect the oxidation solution is obtained by a two stage neutralization of a Caro's acid solution, the first stage to e.g. 0.5 to 2.0 and the second stage to about 7 to 9. In preferred embodiments, the substrate is introduced into partially neutralized Caro's acid, and the second stage neutralization in the presence of the substrate is most preferably carried out with an alkali salt such as sodium bicarbonate. The process can employ relatively low ratios of substrate: Caro's acid oxidant and homogeneous reaction conditions. The process is particularly useful for preparing dioxiranes from ketones.

22 Claims, 2 Drawing Sheets

OXIDATION PROCESS

This application is a 371 of PCT/GB92/01879 filed Oct. 14, 1992.

This invention is concerned with a process for oxidising substrates susceptible to nucleophilic oxidation. More particularly, though not exclusively,. the present invention is concerned with a process for the preparation of dioxiranes by reacting a bicaroate ($HSO_5^-$), obtained from Caro's acid or monopersulphate with a ketone.

Murray et al, J. Org. Chem., Vol. 50, No. 16, 1985, pages 2847 to 2853, discloses a process for the in-situ preparation of dioxiranes by reacting, in a reaction zone, a bicaroate or monopersulphate with acetone. The bicaroate or monopersulphate is added dropwise to an acetone solution (i.e. to a liquid phase which is predominantly organic and potentially having a low flash point), and the dioxirane is produced in a liquid phase solution comprising a low concentration of dioxirane and excess of unreacted acetone. In other papers, such as by Adam et al in J Org Chem 1987, 52, 2800–2803, a carrier gas or reduced pressure is suggested as a means of stripping product from the reaction mixture.

It is an object of the present invention to provide a new or improved oxidation process for substrates susceptible to nucleophilic oxidation.

It is a further object of the present invention to provide a new or improved process for the preparation of a dioxirane.

In accordance with a first aspect of the present invention, there is provided a process for oxidising a substrate susceptible to nucleophilic oxidation by reacting, in a reaction zone, a bicaroate or monopersulphate solution with the substrate and the process is characterised in that the substrate is introduced into the reaction zone in a gaseous phase with a gaseous carrier, which is inert to nucleophilic oxidation, and the oxidised substrate so produced is extracted from the reaction zone in a gaseous phase with the inert gaseous carrier.

In accordance with a second aspect of the present invention, there is provided a process for the oxidation of a substrate susceptible to nucleophilic oxidation by reacting, in a reaction zone, a bicaroate or monopersulphate solution with the substrate and the process is characterised by in Step (a) neutralising an aqueous Caro's acid solution with at least an equimolar equivalent of base in at least two stages, by a process which comprises (1) reacting the Caro's acid with less than an equimolar equivalent of base to form a mixture of bicaroate and Caro's acid, (2) removing a proportion of the heat generated by the reaction of Step (a)(1) from the mixture formed in Step (a)(1), (3) reacting the mixture formed in Step (a)(2) with the remaining amount of base to form a final solution, which solution preferably has a pH of from 7 to 9, more preferably from 7.5 to 8.5; and in Step (b) reacting said substrate with at least partially neutralised Caro's acid solution to form oxidised substrate when the solution has or attains an approximately neutral or alkaline pH.

Substrates suitable for oxidation by the process of the present invention will be apparent to those skilled in the art. Typically, such substrates include ketones, tertiary amines, sulphides and electrophilic olefins.

In accordance with a third aspect of the present invention, there is provided a process for the preparation of a dioxirane by reacting, in a reaction zone, a bicaroate or monopersulphate with a ketone and the process is characterised in that the ketone is introduced into the reaction zone in a gaseous phase with a gaseous carrier, inert to nucleophilic oxidation, and the dioxirane so produced is extracted from the reaction zone in a gaseous phase with the inert gaseous carrier.

In a fourth aspect, the present invention provides a process for the preparation of a dioxirane by reacting, in a reaction zone, a bicaroate or monopersulphate solution with a ketone characterised by in Step (a) neutralising an aqueous Caro's acid solution with at least an equimolar equivalent of base in at least two stages, by a process which comprises (1) reacting the Caro's acid with less than an equimolar equivalent of base to form a mixture of bicaroate and Caro's acid, (2) removing a proportion of the heat generated by the reaction of Step (a)(1) from the mixture formed in Step (a)(1), (3) reacting the mixture formed in Step (a)(2) with the remaining amount of base to form a final solution, which solution preferably has a pH of from 7 to 9, more preferably from 7.5 to 8.5; and in Step (b) reacting said ketone with at least partially neutralised Caro's acid solution to form dioxirane when the solution has or attains an approximately neutral or alkaline pH.

In the figures, ACU is an adiabatic Caro's acid unit in accordance with UK patent application No. 9023433.7.

With respect in particular to the second and fourth aspects of the present invention, in Step (a)(1), it is preferable for the Caro's acid solution to be neutralised to a pH of at least 0.5. Although in principle neutralisation to a mildly acidic pH such as pH 5 can be contemplated in step (a)(1), it is preferable to control the period of time that Caro's acid solution that has been partially neutralised to a mildly acidic pH of for example above pH 3 remains at an elevated temperature. The sensitivity of the Caro's acid solutions to decomposition, with consequential loss of available oxygen, increases both as its pH rises and as its temperature rises. For a continuous process, it is most desirable for step (a)(1) not to exceed a pH of about 2 and for a batch process not to exceed a pH of about 3. By so doing, the combination of hot conditions and only mildly acidic Caro's acid solution is avoided.

Considerable latitude is possible in the first stage neutralisation, especially in batch processes; similar results being attainable with varying strengths of base. The base can comprise an alkali metal hydroxide such as especially sodium hydroxide or an alkali salt of a weaker acid than sulphuric, such as alkali metal carbonate or bicarbonate. A base concentration in the region of between 5 and 15% w/w alkali metal hydroxide and particularly from about 8 to about 12% w/w represents a particularly desirable balance of base concentrations for continuous neutralisation processes, but that can be used in batch neutralisations as well.

It will be understood that, if desired, it is possible to divide the overall neutralisation process into more than two stages, such as an initial stage neutralisation to pH 0.5 to 2.0, one or more intermediate neutralisation stages to a pH from 2.0 to 5.0 and a final stage neutralisation to an alkaline pH. It is preferable for Step (a)(1) and Step (a)(2) to occur simultaneously.

Particularly at or approaching neutral or alkaline conditions, i.e. in step (a)(3) it is especially desirable to control the pH of the solution closely, e.g. by incorporating a buffer either as the base or in conjunction with a base.

Figure 1:
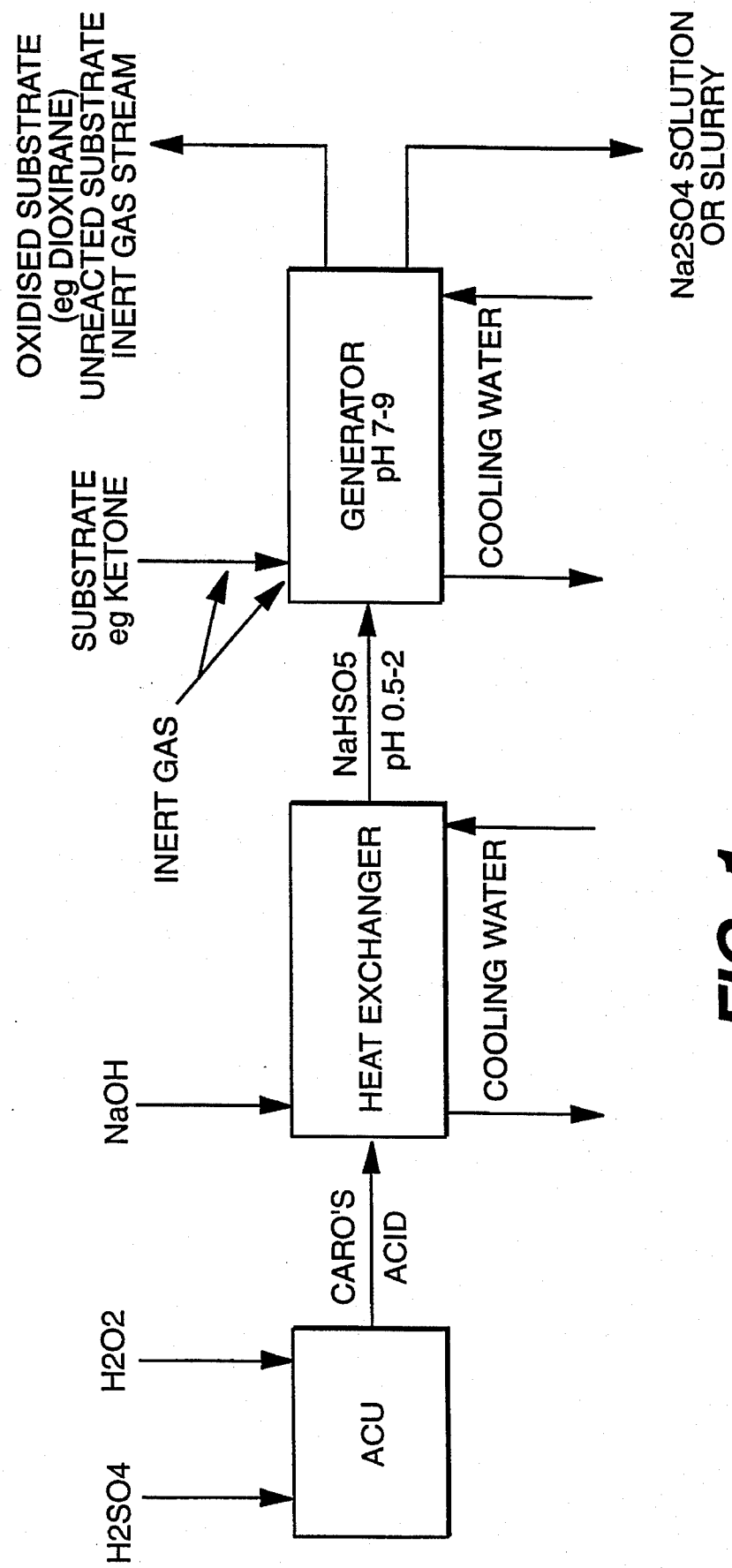
FIG. 1 is a schematic outline of a preferred process in accordance with the present invention in which the substrate is introduced simultaneously with the neutralizer.
Figure 2:
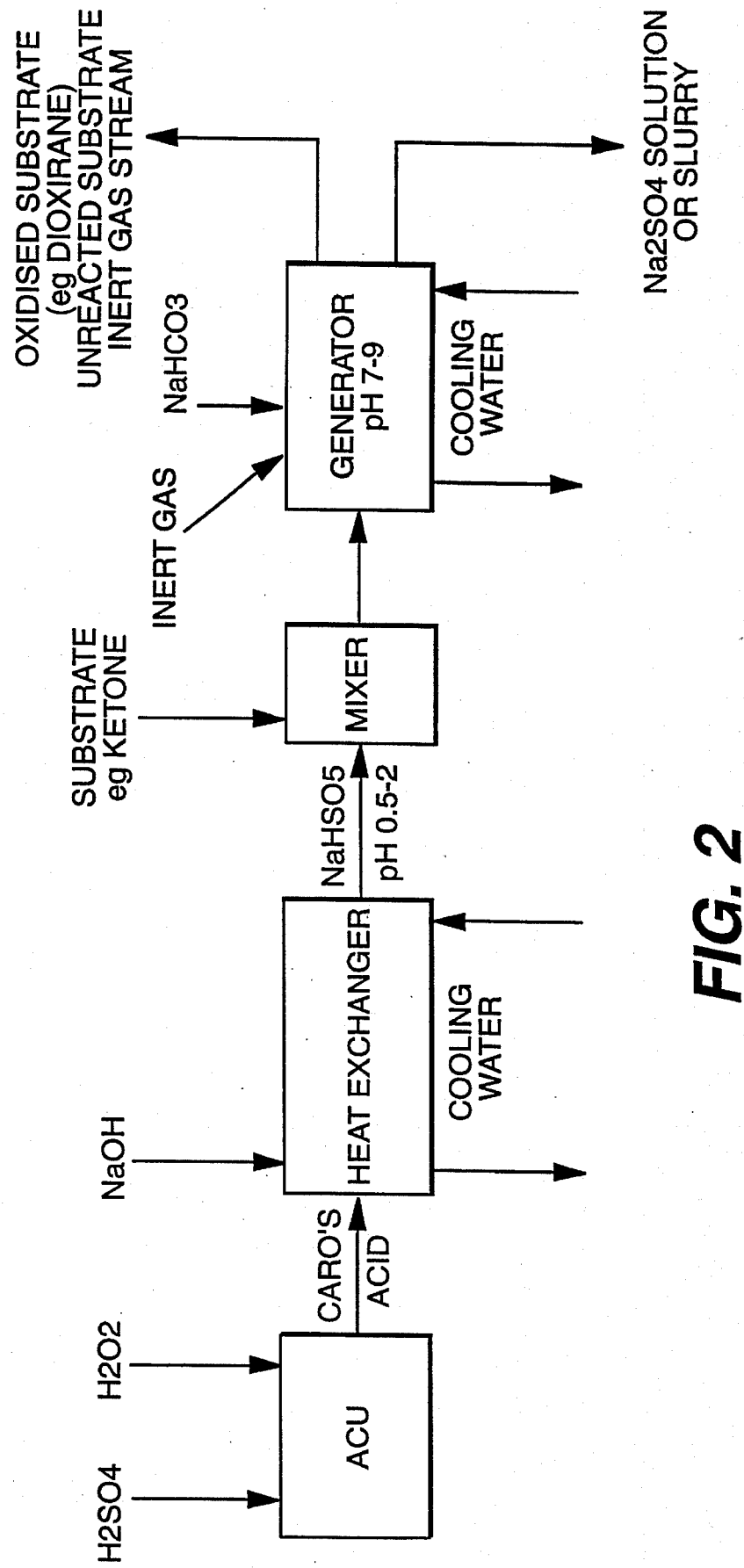
FIG. 2 is a schematic outline of a second preferred process in accordance with the present invention in which ketone is introduced into partially neutralized Caro's acid solution.

Preferably, Step (b) in the second and fourth aspects is initiated before or immediately after Step (a)(3) is initiated. In fact, in a number of variations employing a continuous process, the process steps(b) and (a)(3) effectively occur simultaneously, such that the addition of base serves to control the pH between the prescribed alkaline limits for formation of oxidised substrate, such as dioxirane. (FIG. 1) In alternative and very convenient variations, the introduction of the substrate such as a ketone inherent in process step (b) precedes (a)(3) or the stage of (a)(3) in which the solution pH becomes approximately neutral or alkaline (FIG. 2). In such process variations, the substrate is desirably introduced into a Caro's acid solution having a pH of from about 0.5 to 5 and especially from about 0.5 to about 2. It is most preferred for Step (a)(1) and Step (a)(2) to occur simultaneously and for Step (a)(3) and Step (b) to occur simultaneously, by virtue of the substrate being present before introduction of the neutraliser commences or with simultaneous introduction of the step (a)(3) neutraliser and substrate.

In the first and third aspects of the present invention and in some preferred embodiments of the second and fourth aspects, the substrate, and in particular a ketone, is in the form of a vapour which is bubbled into the neutral solution. The substrate vapour preferably additionally comprises a carrier gas which is inert to nucleophilic oxidation. The carrier gas, along with assisting introduction of the substrate to the reaction mixture, is preferably used to strip the oxidised substrate from the reaction mixture formed in Step (b).

In other embodiments of the second and fourth aspects, and in particular those in which a ketone substrate is introduced into partially neutralised Caro's acid solution, it is introduced in the form of a solution. In such pH conditions, it is believed that the substrate interacts with the Caro's acid or anion to form an intermediate from which oxidised substrate is generated when the pH of the solution is rendered approximately neutral or alkaline in step (a)(3). It will be recognised that by introducing the substrate, e.g. ketone, into the aqueous part neutralised solution rather than the other way round, the proportion of organic material in the reaction mixture is minimised at all times.

When neutralisation to alkaline pH is effected in the presence of the substrate, and particularly a ketone, either by simultaneous addition of substrate and neutraliser or prior addition of substrate, it is highly desirable to control the pH of the solution within tight limits, for example by employing a weak base as the neutraliser, such as alkaline carbonate and/or bicarbonate. The yield of oxidised substrate, such as dioxirane, is thereby improved.

The oxidised substrate can be recovered from the neutralised Caro's acid solution conveniently using an inert carrier gas such as nitrogen or a predominantly nitrogen mixture and/or by subjecting the solution to a partial vacuum.

The gaseous mixture extracted from the reaction zone comprises dioxirane, optionally inert carrier and a proportion of unreacted or reformed ketone. However, the process of the present invention provides the advantage that the dioxirane concentration in the gaseous mixture is substantially higher than that obtainable in the Murray liquid-phase prior art process. Furthermore, the gaseous mixture comprises relatively lower ketone concentrations than the liquid-phase prior art process, which is especially useful in recycled systems as a reduced ketone inventory is advantageous. These advantages, when combined, proffer reduced production and handling costs for dioxiranes over the costs incurred with the prior art process.

The introduction of ketone substrate into partially neutralised Caro's acid solution enables the stage of introduction of substrate to be separated from the stage at which dioxirane product is recovered from the reaction mixture, thereby permitting the conditions for each stage to be tailored to its respective needs.

Caro's acid is often produced by the reaction of sulphuric acid with hydrogen peroxide. A most suitable method for the preparation of Caro's acid is described in UK Patent Application No. 9023433.7, filed 23rd September 1990, corresponding to International Patent Application Publication No WO 92/07791. For the purposes of the present invention, it is advantageous to use Caro's acid with a low residual hydrogen peroxide content, such as that produced by equilibration of a mixture of at least an equimolar amount of concentrated sulphuric acid, preferably at least 94% w/w and often from 94 to 99% w/w with concentrated hydrogen peroxide, preferably at least 60% w/w and often from about 65% to 85% w/w. Especially suitable processes employ an $SO_3:H_2O_2$ mole ratio of from about 1.5:1 to about 4:1, in which convenient mole ratios are about 1.5:1. 2:1 and 3:1, and widely available reactants comprise 98% sulphuric acid and 70% hydrogen peroxide. Other suitable processes for the preparation of Caro's acid are described in GB-A-738407, U.S. Pat. No. 3,900,555 and U.S. Pat. No. 3,939,072. It is preferred to use neutralised Caro's acid in all aspects of the present invention. Monopersulphate salts may also be used in the first and third aspects of the present invention instead of bicaroate, which monopersulphates may be obtained from potassium monopersulphates of the formula $2KHSO_5.KHSO_4.K_2SO_4$ or $KHSO_5.H_2O$. Partially neutralised solutions thereof can be obtained by dissolution with or without acidification.

In one preferred embodiment of the process of the present invention, a stream of vaporised ketone, with an inert gaseous carrier e.g. nitrogen, is passed through the neutralised bicaroate or monopersulphate solution when a proportion of the ketone reacts with the bicaroate or monopersulphate to form a dioxirane, which is stripped from the reaction mixture by the carrier gas. The carrier gas, dioxirane and some unreacted ketone is then extracted from the reaction vessel. The process is preferably carried out as a continuous process, though conduct as a batch process is also possible. In a more preferred embodiment, the ketone stream is passed through the neutralised bicaroate or monopersuiphate solution as the solution is being formed, i.e. in a manner equivalent to the combining of Steps (a)(3) and (b) described hereinabove and employing sodium carbonate and/or bicarbonate solution as neutraliser in that Step.

The following formulae represent the overall reactions believed to be carried out in the above processes when a ketone is employed as substrate:

Steps (a)(1) and (a)(2):

$$H_2SO_4+yH_2SO_5+(2x+y)NaB \rightarrow xNa_2SO_4+yNaHSO_5+(2x+y)HB$$

Steps (a)(3) and (b):

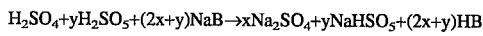
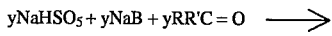
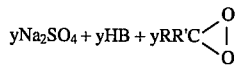

where B is a basic anion such as $^-OH$, $0.5(CO_3^{2-})$ or $HCO_3^-$, R and R' are independently $(C_1-C_6)$ alkyl groups or R and R' together with the carbon which is or has been subjected to nucleophilic attack form a $(C_3-C_8)$cycloalkyl group, preferably a cyclohexyl group. The formulae demonstrate the oxidation of a ketone, but analogous reactions are believed to be followed for other substrates susceptible to nucleophilic oxidation.

When sodium sulphate is formed as a by-product, the by-product is preferably subjected to electrolytic regeneration in a membrane cell to provide caustic and sulphuric acid which are then available for reuse in the process of the present invention.

The reaction of the substrate (especially ketone) with bicaroate or monopersulphate can be carried out at a pressure of from about 5 mBar to about 10 Bar, and is preferably carried out under atmospheric pressure at about −20° to 70° C., preferably 20° to 50° C. It is an advantageous feature arising from the characteristics of the invention process that it can be carried out at ambient or slightly elevated temperatures in reasonable safety, thereby obviating any need to cool the reaction mixture to subambient temperatures that must be contemplated if a flammable chemical having a low flash point, like acetone, is deployed as the principal component of a liquid phase into which oxidant is introduced.

The ratio bicaroate:substrate(preferably ketone) in the reaction zone is preferably 1:1 to 50, and particularly in the range 1:2 to 20, on a molar basis in some processes according to the present invention. In certain other process variations, the mole ratio of bicaroate/permonosulphate:ketone substrate is selected in the region of about 1:30 to 50. In yet other variations, said ratio of oxidant:ketone substrate is chosen in the range of 1:50 to 100, in which two latter regions, the concentration of dioxirane in ketone solvent removed from the reaction mixture is found in the region of about 0.06 to about 0.18 mol/dm$^3$, whilst employing a comparatively low ratio of permonosulphate oxidant to substrate, thereby achieving a relatively effective usage of the oxidant on a molar basis.

In the prior art process, the ratio dioxirane:ketone has been found to be 1:90 to >500. In at least some embodiments of the present invention, a significantly improved dioxirane:ketone ratio can be attained. It is advantageous to have a low ketone concentration in these mixtures, in order to make possible a greater percentage conversion of substrate to oxidised substrate and to reduce thereby the substrate inventory. In addition, the invention process enables a homogeneous reaction mixture to be obtained and employed, thereby obviating the practical difficulties of the heterogeneous system that could occur with use of a slurry of a solid persulphate on a large scale.

The concentration of dioxirane in ketone the extracted product mixture obtained by inert gaseous stripping or under partial vacuum is often at least 0.06 mol/dm$^3$, in many process variations greater than 0.1 mol/dm$^3$, and particularly from about 0.12 to about 0.18 mol/dm$^3$.

In a preferred embodiment of the present invention, a monopersulphate and/or bicaroate solution having a pH of approximately pH 7 or higher is prepared by reacting Caro's acid, having a concentration of 1 to 50% with an aqueous base solution such as sodium hydroxide, or other appropriate base such as sodium carbonate or bicarbonate, having a preferred concentration of 2 to 50%. However, in instances, the concentration of base is selected in the region of about 5 to 15% w/w and particularly from about 8 to 12% w/w. The neutralisation process is effected in a stagewise procedure, preferably in two stages. In the first stage, a deficiency of base such as sodium hydroxide is initially used to generate a bicaroate solution that is relatively stable, preferably at a pH of not greater than about 2, until the solution has cooled or has been cooled to that temperature required for dioxirane generation. When the appropriate temperature is reached, the neutralisation is continued, preferably with excess base, selected in accordance with whether substrate is present or absent. The pH of the neutralised solution is preferably pH 7.5±0.5.

Dioxiranes manufactured or prepared in accordance with the present invention have many different uses, for example those uses described by Murray et al in J. Org. Chem., Vol. 50, No. 16, 1985, pages 2847 to 2853, by Murray in Chem. Rev. 1989,89,1187–1201, and by Adam et al in Acc. Chem. Res., 1989,22,205–211. The dioxiranes may be used for bleaching and/or delignifying lignocellulosic materials. Typically, the bleaching process is as described in PCT Patent Application WO 91/12369, which is hereby incorporated by reference.

Specific embodiments of the invention will now be described in greater detail by way of example only. For use in the Examples, Caro's acid feedstocks were prepared by mixing aqueous solutions containing respectively 98% w/w sulphuric acid and 70% w/w hydrogen peroxide in a mole ratio of $SO_3:H_2O_2$ of 1.7:1 under controlled temperature conditions with cooling to produce after equilibration a solution containing approximately 40% w/w permonosulphuric acid. Just prior to use, the actual peracid content was determined by a standard titration against 0.1M ceric sulphate for hydrogen peroxide and N/10 thiosulphate for $H_2SO_5$.

EXAMPLE 1

In this Example, a Caro's acid solution containing 40.9% w/w $H_2SO_5$ (25.7 g) was neutralised in a batch manner by introduction over a period of 90 minutes with vigorous mixing and cooling of an aqueous 10% w/w solution of NaOH under the control of a pH probe until the solution had attained a pH of 1.5, a total of 136.6 g sodium hydroxide solution. 160 g of the partially neutralised Caro's acid solution at approximately ambient temperature (about 22° C.) was transferred to a three necked flask, acetone (4.6 g) was introduced and the mixture was stirred for 30 minutes. An aqueous solution of sodium bicarbonate (10 g 142 g water) was introduced which altered the pH to 7.7. The pressure was lowered to approximately 23 inches Hg (about $7\times10^4$ Pa) for 10 minutes and the gaseous strippings passed through a dry ice trap. The recovered product comprised 2 mls approx of a solution of dimethyldioxirane (0.13 mol/dm$^3$—DMD) in acetone, determined by titration against N/100 thiosulphate.

EXAMPLE 2

Similar DMD concentrations were obtained when Example 1 was repeated on an approximately 8 x scale, employing about 136 g NaOH solution in the first step neutralisation, 32.2 g acetone and 14.11 g sodium bicarbonate in the second step neutralisation. 25 mls of solution were obtained having a DMD concentration of 0.12 mol/dm$^3$.

EXAMPLES 3 and 4

Example 2 was repeated except that the mixture of acetone and partially neutralised Caro's acid was held respectively overnight or 3 hours before the second neutralisation step. Respectively 25 mls and 31 mls of product were recovered, each having a DMD concentration of 0.15 mol/dm$^3$.

EXAMPLE 5

In this Example, a Caros acid solution containing 40.15% w/w $H_2SO_5$ was partially neutralised in a first step to pH 1.5 in a first stage by mixing with a 10% w/w solution of sodium hydroxide, 130.93 g, and cooled to ambient temperature. In a second step, 156.6 g of the partially neutralised solution was transferred into a reaction vessel, and two liquids were introduced with stirring, acetone (32.2) and a solution of 10 g NaHCO$_3$ in water (142 g). The mixture attained a pH of 7.5. Product was removed from the solution under a vacuum of about 26 inches Hg (pressure of about $8 \times 10^4$ Pascals) and a total of 21 mls of solution was trapped by a dry ice trap in 10 minutes, having a concentration of 0.14 mol/dm$^3$ DMD.

Trial 6

In this trial, Example 5 was repeated, except that the sodium bicarbonate solution was replaced by a 3% w/w solution of sodium hydroxide in water, 105.7 g. The acetone-containing mixture attained a final pH of 7.7. The product was recovered in exactly the same way as in Example 5, but the 21 mls had a concentration of only 0.0115 mol/dm$^3$ DMD. The comparison with Example 5 shows the importance of selecting a buffer-base such as sodium bicarbonate for the second step neutralisation to alkaline conditions.

EXAMPLE 7

In this Example the procedure of Example 5 was followed, except that in the first neutralisation step, a 30% w/w solution of sodium hydroxide was employed instead of the 10% solution. The product isolated by the dry ice comprised 25 mls having a DMD concentration of 0.12 mol/dm$^3$.

EXAMPLE 8

In this Example, the procedure of Example 1 was followed, except that the product was recovered from the neutralised Caro's acid solution by passage of a stream of nitrogen bubbled through the solution from a ring of gas inlets close to the bottom of the solution container. The dry ice trap yielded 2 ml of acetone solution containing DMD at a concentration of 0.06 mol/dm$^3$.

EXAMPLE 9

In this Example, the procedure of Example 8 was followed, with the exception that the solution of acetone in partially neutralised Caro's acid at pH 1.5 was dripped into the solution of sodium bicarbonate (10 g in 142 g water) over a period of 20 minutes whilst the mixture was purged with nitrogen. Purging with nitrogen continued for a further 5 minutes, and 3 mls of product was recovered containing DMD at 0.12 mol/dm$^3$.

EXAMPLE 10

In this Example, the procedure of Example 9 was followed, except that acetone was introduced into the reaction mixture in a stream of nitrogen (3000 ml/min) rather than in liquid form. The nitrogen gas was loaded with acetone by bubbling through a bath of acetone, 10 g. The nitrogen stream was employed for 10 minutes, thereby introducing 3.8 g of acetone into the reaction mixture. The recovered product comprised 3 mls approx of a solution of dioxirane (0.03 mol/dm$^3$) in acetone.

EXAMPLE 11

In this Example, a Caro's acid feedstock (500 ml, 40.1% w/w H$_2$SO$_5$, was pumped through a mixing chamber having a cooling jacket through which glycol was pumped to provide a temperature of about 3° C., at a rate of approximately 22.9 g/min. A sodium hydroxide solution (10% w/w) was pumped into the mixing chamber at a rate of 129 g/min and the resultant mixture had a pH of 1.5. The pH was adjustable via a feedback control mechanism in which a pH detector in the partially neutralised solution was linked to a flow control valve in the neutraliser feed line. The partially neutralised mixture flowed through a second cooling chamber and reached about 29° C. A sample of 160 g was then employed in a second stage neutralisation process according to Example 1, together with acetone, 4.8 g and sodium bicarbonate, 10 g in 142 g water. A product was recovered comprising 3 mls of solution of 0.11 mol DMD/dm$^3$.

EXAMPLE 12

In this Example, a partially neutralised Caro's acid solution (19.3 g containing 8.4% w/w NaHSO$_5$ having a pH of 1.5 was obtained by the method of Example 1. Sodium bicarbonate, (3.0 g), water, (20 g) and acetone (40 g) were charged into a three necked flask and the Caro's acid solution introduced gradually over 15 minutes. The resultant mixture had a pH of 7.3. The pressure in the vessel was lowered to 24 in Hg and a total volume of acetone solution was and trapped by dry ice. The product had a concentration of 0.075 mol DMD/dm$^3$. Thus in this Example the Caro's acid solution was more efficient than in previous Examples at generating DMD.

In a repeat of this Example, in which 100 ml water was present in the mixture, a similar recovery was observed.

Comparison 13

In this Comparison, a solution of acetone (16.25 g) and sodium carbonate (7.9 g) in water (153 ml) was stirred at ambient temperature in a 3-necked round bottomed flask. Potassium permonosulphate triple salt available under the Trade Mark "Oxone" (16.25 g) was introduced via a pressure equalized solids addition funnel into the stirred mixture during 15 minutes. The resultant pH of the mixture was 7.4. Product comprising DMD in acetone was then recovered from the mixture under a vacuum of 80 torr and collected by trapping using dry ice as in preceding Examples. After 15 minutes pumping, 7 ml of product was obtained having a molarity of 0.03 mol/dm$^3$.

We claim:

1. A process for the oxidation of a substrate susceptible to nucleophilic oxidation by reacting, in a reaction zone, a monopersulfate with the substrate which comprises the following steps:

(a) neutralizing an aqueous Caro's acid solution with at least an equimolar equivalent of base in said reaction zone by a process which comprises (1) reacting aqueous Caro's acid solution with less than an equimolar equivalent of base in said reaction zone to form partially neutralized Caro's acid solution containing monopersulfate and generate heat, (2) removing a portion of said heat generated in step (a)(1) to form cooled partially neutralized Caro's acid solution in said reaction zone, and (3) reacting said cooled partially neutralized Caro's acid solution with additional base in said reaction zone to fully neutralize the Caro's acid and form a final solution, which final solution has a pH of from 7 to 9, and wherein the total amount of base in steps (a)(1) and (a)(3) is equal to said at least equimolar equivalent; and (b) introducing said substrate into said reaction zone during step (a) when the aqueous Caro's acid solution is at least partially neutralized and thereby contains monopersulfate, and reacting said substrate and said monopersulfate in said reaction zone at an approximately neutral or alkaline pH to form oxidized substrate.

2. A process for the preparation of a dioxirane by reacting, in a reaction zone, a monopersulfate with a ketone substrate which comprises the following steps:

(a) neutralizing an aqueous Caro's acid solution with at least an equimolar equivalent of base in said reaction zone by a process which comprises (1) reacting aqueous Caro's acid solution with less than an equimolar equivalent of base in said reaction zone to form partially neutralized Caro's acid solution containing monopersulfate and generate heat, (2) removing a portion of said heat generated in step (a)(1) to form cooled partially neutralized Caro's acid solution in said reaction zone, and (3) reacting said cooled partially neutralized Caro's acid solution with additional base in said reaction zone to fully neutralize the Caro's acid and form a final solution, which final solution has a pH of from 7 to 9, and wherein the total amount of base in steps (a)(1) and (a)(3) is equal to said at least equimolar equivalent; and (b) introducing said ketone substrate into said reaction zone during step (a) when the aqueous Caro's acid solution is at least partially neutralized and thereby contains monopersulfate, and reacting said substrate and said monopersulfate in said reaction zone at an approximately neutral or alkaline pH to form dioxirane.

3. A process according to claim 1 or 2, characterized in that the final solution produced in step (a)(3) has a pH of from 7.5 to 8.5.

4. A process as claimed in claim 1 or 2, wherein step (a)(1) and step (a)(2) occur simultaneously.

5. A process as claimed in claim 1 or 2 characterized in that the partially neutralized Caro's acid solution in step (a)(1) has a pH of from 0.5 to 2.0.

6. A process according to claim 1 or 2, characterized in that the substrate is introduced into partially neutralized Caro's acid solution having a pH of from 0.5 to 5.0 and said pH is thereafter adjusted in step (a)(3) to a pH from 7 to 9.

7. A process according to claim 1 or 2, characterized in that step (a)(3) and step (b) occur simultaneously.

8. A process as claimed in claim 1 or 2, characterized in that in step (a)(3), the base is an alkali bicarbonate.

9. A process as claimed in claim 1 or 2, characterized in that the substrate is introduced into the at least partially neutralized Caro's acid solution in the form of liquid.

10. A process as claimed in claim 1 or 2, characterized in that the substrate is introduced in the form of a vapor which is bubbled into the at least partially neutralized Caro's acid solution.

11. A process as claimed in claim 10, wherein the substrate vapor is introduced with a carrier gas which is inert to nucleophilic oxidation conditions.

12. A process as claimed in claim 1, characterized in that an inert carrier gas is used to strip the oxidized substrate from the reaction zone approximately neutral or alkaline pH conditions.

13. A process as claimed in claim 1, characterized in that the substrate to be oxidized is a tertiary amine, sulphide or electrophilic olefin.

14. A process according to claim 2, characterized in that the base in step (a)(3) is sodium carbonate and/or bicarbonate.

15. A process as claimed in claim 2, wherein the reaction of the ketone and at least partially neutralized Caro's acid solution is carried out at −20° to 70° C.

16. A process according to claim 15, wherein the reaction is carried out at 20° to 50° C.

17. A process as claimed in claim 2, wherein the ratio of monopersulphate:ketone in the reaction zone is 1:1 to 50, on a molar basis.

18. A process as claimed in claim 17, characterized in that the ratio of monopersulphate:ketone in the reaction zone is 1:2 to 20, on a molar basis.

19. A process as claimed in claim 2, wherein the ratio of monopersulphate:ketone in the reaction zone is 1:50 to 100, on a molar basis.

20. A process as claimed in 2, characterized in that an inert carrier gas is used to strip the dioxirane from the reaction zone under approximately neutral or alkaline conditions.

21. A process for oxidizing a substrate susceptible to nucleophilic oxidation by reacting, in a reaction zone, a monopersulphate solution with the substrate and the process is characterized in that the substrate is introduced into the reaction zone in a gaseous phase with a gaseous carrier which is inert to nucleophilic oxidation conditions and the oxidized substrate so produced is extracted from the reaction zone in a gaseous phase with the inert gaseous carrier.

22. A process for the manufacture of a dioxirane by reacting, in a reaction zone, a monopersulphate solution with a ketone characterized in that the ketone is introduced into the reaction zone in a gaseous phase with a gaseous carrier, which is inert to nucleophilic oxidation conditions, and the dioxirane so produced in extracted from the reaction zone in a gaseous phase with the inert gaseous carrier.

* * * * *